US00PP33510P3

(12) United States Plant Patent
Maillard et al.

(10) Patent No.: US PP33,510 P3
(45) Date of Patent: Sep. 28, 2021

(54) PEACH TREE NAMED 'FLATRUMBA'

(50) Latin Name: ***Prunus persica* (L.) Batsch**
Varietal Denomination: FLATRUMBA

(71) Applicant: AGRO SELECTIONS FRUITS, Elne (FR)

(72) Inventors: Laurence Maillard, Elne (FR); Arsène Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 76 days.

(21) Appl. No.: 16/602,679

(22) Filed: Nov. 20, 2019

(65) Prior Publication Data

US 2020/0178442 P1 Jun. 4, 2020

(30) Foreign Application Priority Data

Nov. 29, 2018 (QZ) ..... 2018/3134

(51) Int. Cl.
*A01H 5/08* (2018.01)
*A01H 6/74* (2018.01)

(52) U.S. Cl.
USPC ..... Plt./195
CPC ..... *A01H 6/7463* (2018.05)

(58) Field of Classification Search
USPC ..... Plt./195, 188, 198
CPC ... A01H 5/08; A01H 5/00; A01H 6/74; A01H 6/7463; A01H 6/7427; A01H 5/02
See application file for complete search history.

(56) References Cited

PUBLICATIONS

Upov Pluto Plant Variety Database 20200526 retrieved on May 28, 2020, retrieved from the Internet at https://www.upov.int/pluto/en/index.jsp, one page. (Year: 2020).*

* cited by examiner

*Primary Examiner* — June Hwu
(74) *Attorney, Agent, or Firm* — Birch, Stewart, Kolasch & Birch, LLP

(57) ABSTRACT

A new and distinct variety of white flat peach tree denominated 'FLATRUMBA' which have fruits with high eating quality and very long shelf life without alteration before and after harvesting, with a semi-sweet white or cream white flesh, a red pigmentation into and around the stone cavity, and an attractive skin with a high percentage of luminous purple red blush on skin surface, on a washed red background.

3 Drawing Sheets

Botanical classification: *Prunus persica* (L.) Batsch.

Variety denomination: 'FLATRUMBA'.

This application claims priority of Community plant variety right No. 2018/3134 filed on Nov. 29, 2018 which is hereby incorporated by reference in its entirety.

The new variety named 'FLATRUMBA' is also known as 24.05.87.15 PBPL or ASF15245. Indeed, before giving a name to a new and distinct variety of fruit tree, a provisional reference is assigned, considering the references of a tree in orchard. This provisional reference is constituted firstly with the number of the parcel on which the tree has grown, then the number of the line, the tree number and finally the year of selection. Then before being named 'FLATRUMBA', the provisional reference of this white flat peach tree variety was 24.05.87.15, corresponding to the tree 87 located in line 05 of the parcel 24 and selected during the year 2015. The letters "PBPL" are related to the first letters of the type of tree in French (PBPL for "Pêche Blanche PLate", that means "white flat peach"). Once the hybrid selected, the breeder assigned a clone reference that begins with the letters "ASF" followed by the year of selection and a number corresponding to the maturity order. The final name is only assigned once the application has been filed and the name approved after its publication in the official bulletin. For the variety 'FLATRUMBA', the clone reference was 'ASF15245'.

BACKGROUND OF THE NEW VARIETY

The present invention relates to a new and distinct variety of white flat peach tree, *Prunus persica* (L.) Batsch, which has been given the variety denomination 'FLATRUMBA'.

This new tree produces fruits with a long shelf life without alteration both on the tree after growth completion and after harvesting, very good eating quality, semi-clingstone white flesh fruits, generally with a red pigmentation around and into the stone cavity, for fresh market at the end of August or in September in the Pyrénées-Orienteles department, France.

ORIGIN OF THE VARIETY

The 'FLATRUMBA' white flat peach tree originated from a cultivated area of the south of France, in the Pyrénées-Orientales department, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year and are mostly found in Spring and Autumn. In May and October, very intense precipitations occasionally happen. Summer is dry with a few thunderstorms.

The 'FLATRUMBA' variety results from pollinated cross between the white nectarine variety named 'NECTARBONDANT' (U.S. Plant Pat. No. 23,458) which was used as the seed parent, or female parent, and the white flat nectarine variety named 'CAKEDELICE' (U.S. Plant Pat. No. 25,632) which was used as the pollen parent, or male parent.

The 'FLATRUMBA' variety was obtained by hybridizing and propagated by grafting on a 'INRA GF677' (non-patented) rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting. Every known type of grafting adapted to the peach tree may be performed on the new tree. Especially, the type of grafting will depend on the grafting period and the propagation mode which is used by the nursery owner. Thus, the grafting period may be micrografting at any moment of the year if the grafting is performed in greenhouse, dormant eye shield budding in August or September, growing eye shield budding in June or July, for example.

SUMMARY OF THE VARIETY

The new and distinct variety 'FLATRUMBA' white flat peach tree blooms at the end of February or early in March near Elne in the Pyrénées-Orientales department, France. The blooming period is considered medium. However, it was observed that its date of blooming seems to be highly dependant on climatic conditions.

The first fruit of 'FLATRUMBA' ripens generally late in the season, namely at the end of August. More particularly, ripening time usually begins between August 21$^{st}$ and September 2$^{nd}$. However, it was observed that its date of maturity seems to be highly dependant on climatic conditions.

DESCRIPTION OF THE DRAWINGS

In the accompanying drawing, which are as nearly true as it is reasonably possible to make in a color illustration of this type.

Figure 1:
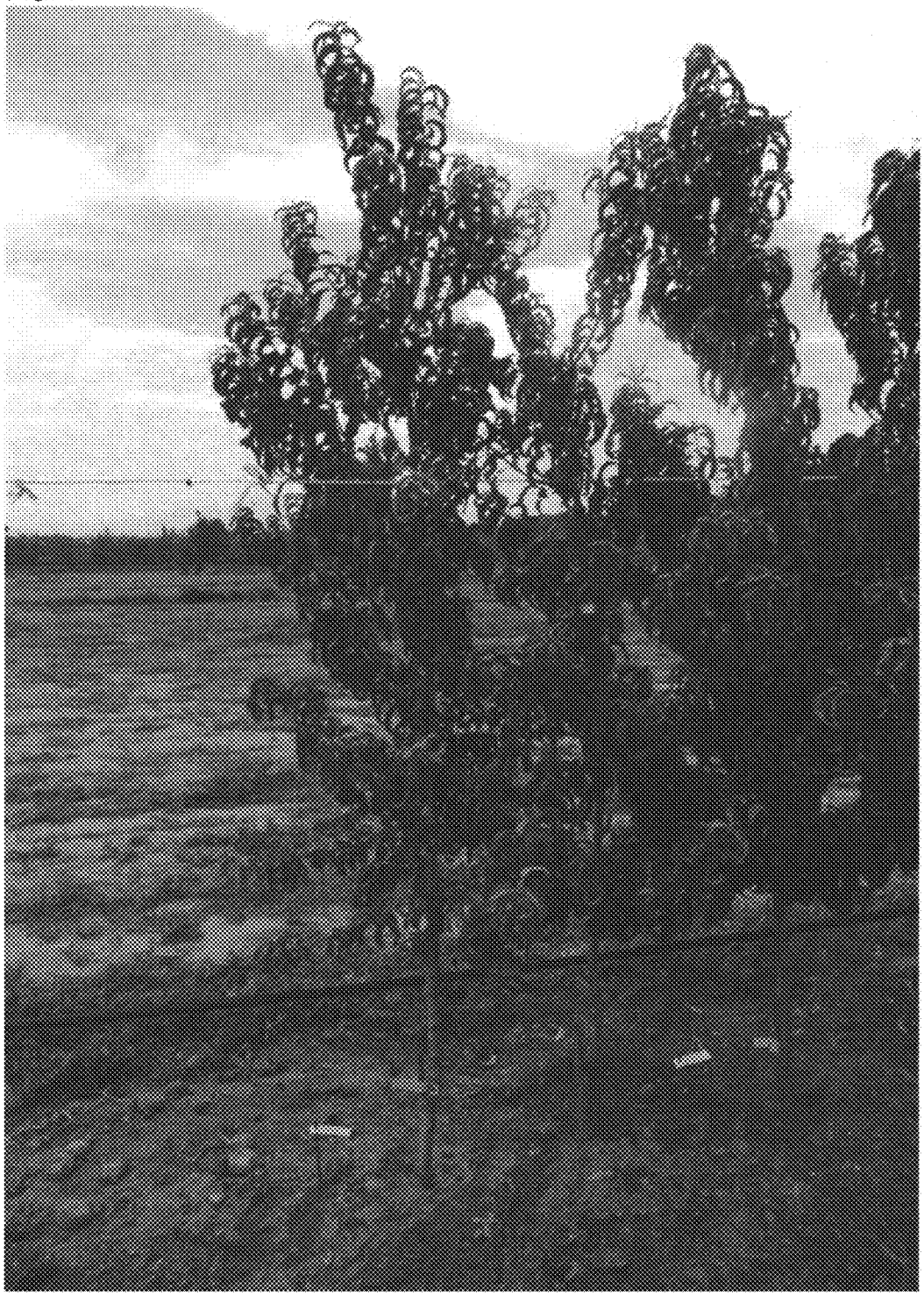
FIG. 1 is a color photograph showing a tree of the new variety in orchard.
Figure 2:
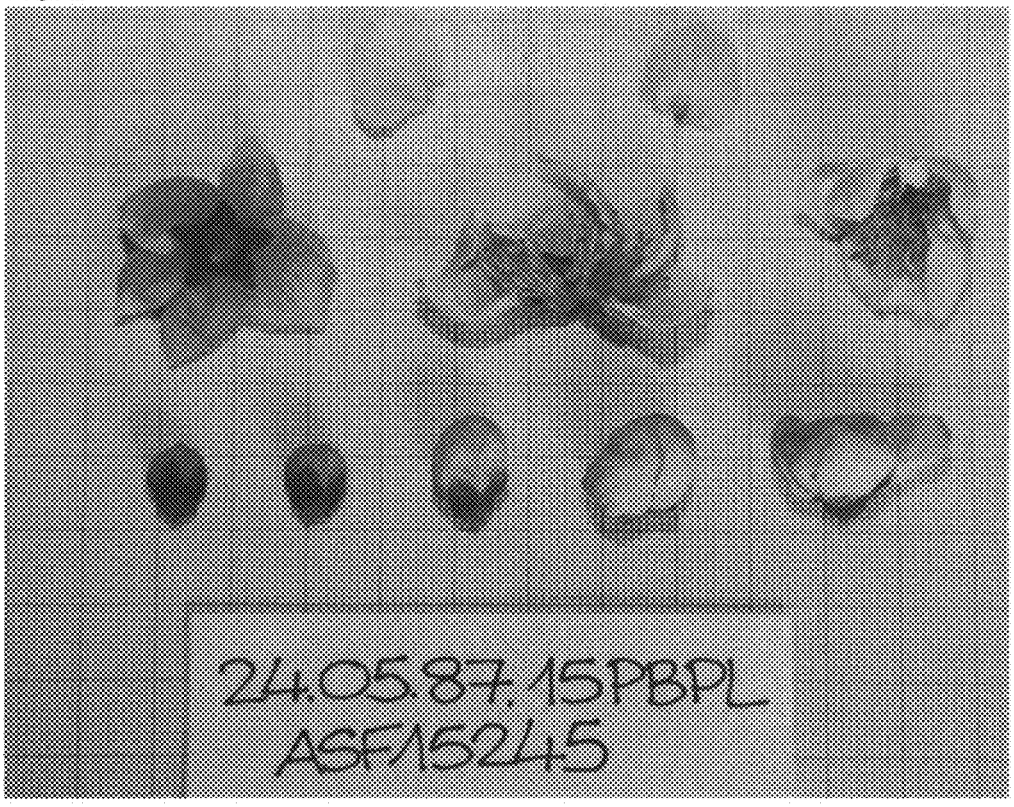
FIG. 2 is a color photograph which depicts the flower buds at different development stages, and the reverse and side view of the flower and the reproductive organs with petals removed, of the new variety 'FLATRUMBA' which is also referenced '24.05.87.15 PBPL ASF15245' by the breeder.

The views of trees, leaves and fruits have been photographed in their third growing season (second year of production). The views of flowers have been photographed in their second growing season (first year of production).

Due to chemical development, processing and printing, the flowers, stones and fruits depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruits by 'FLATRUMBA' is high, due to fruit very long shelf life without alteration after harvesting.

Trees are medium vigorous and large stature half-standing in a semi-flared out aspect. The anthocyanic coloration of flowering shoot is present excluding brushwood side away from sun. The time of beginning of flowering is considered medium; flowering begins at the end of February or early in March. The type of flower is showy (rosette) with medium petal size. Petals are dark pink. Leaf glands are present and round. The fruit flesh is white or cream and generally with a red pigmentation into the stone cavity and in a star shape around the stone cavity, on approximately 5.0 to 6.0 millimeters. The fruit skin is medium thick, with a purple red blush on a washed red background. The stone is semi-clingstone and its size is small. Fruit taste is semi-sweet, very aromatic and with a high level of sugars.

Compared to 'FLATMOON' white flat peach variety (not patented), the fruits of 'FLATRUMBA' ripen approximately 2 weeks earlier. The fruit skin of the new variety 'FLATRUMBA' is colored with a luminous pink red blush covering at least 75% of the skin surface. In comparison, the fruits of 'FLATMOON' are less colored. The red blush covers 75% of the surface on a cream pink background. The closing of the pistil cavity is better in the 'FLATRUMBA' fruits, in comparison with the fruits of the 'FLATMOON' variety. The fruits of 'FLATRUMBA' are bigger that the fruits of 'FLATMOON' as the size is considered 3A for 'FLATRUMBA' whereas for 'FLATMOON' fruits are smaller as the size is considered 2A.

More particularly, in European Regulation related to commercialization of fruits, size 2A corresponds to fruits having a diameter between 73 and 80 mm, whereas size 3A corresponds to fruits having a diameter between 80 and 90 mm. Generally speaking, fruits having size 2A or 3A are considered as large to very large fruits.

DETAILED DESCRIPTION

Referring more specifically to the pomological details of this new and distinct variety of white flat peach tree, the following was observed on trees in their third growing season (second year of production) for leaves and fruits and on trees in their second growing season (first year of production) for the trees and flowers under the ecological conditions prevailing at the orchards located near the town of Elne, Pyrénées-Orientales departement, France. All observations have been done on rootstock cultivars. Used rootstocks were 'INRA GF677' (non-patented) trees. All major color code designations are by reference to The R.H.S. Colour Chart (Fourth Edition) provided by The Royal Horticultural Society of Great Britain.

Tree:

*Size.*—

*Generally.*—Considered large. The tree size the first year was approximately 200 to 280 cm. The tree was pruned during each following dormant season to a height of approximately 250 cm. Current season shoots growth could reach 80 cm. The tree size from the second year (second and next years) reached a final height of 330 cm including current season shoots length. The tree size is consistently reduced to 250 cm the next years.

*Spread.*—Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

*Vigor.*—Considered medium.

*Productivity.*—Considered good to very good, and regular. Fruit set is spaced by thinning to develop the remaining fruit into the desired market sized fruit. The number of the fruit set varies with the prevailing climatic conditions and cultural practices employed during the bloom period and is therefore not distinctive of the present variety. A reduce vegetation, obtained with pruning or green pruning, approximately 1 month or 1 month ½ before harvesting flat fruits, significantly promotes fruit qualities, especially growth, color and firmness. Moreover, contamination risks due to *Monilia* or rot are significantly reduced. 'FLATRUMBA' variety is not much sensitive to cracking of pistil cavity, to cork formation into peduncle cavity or to *Monilia* (*Monilia fructicola*).

*Bearer.*—Very regular. The fruit distribution is considered homogenous on mixed branches and spurs having more than 1 year. Thinning of 2 fruits out of 3 was necessary for the tree valorisation. Thinning was necessary every year during the years of observation.

*Form.*—The 'FLATRUMBA' variety has naturally a semi-flared shape.

*Foliage density.*—Considered dense.

*Hardiness.*—The present tree was grown and evaluated in France. The variety appears to be hardy under the central Pyrénées-Orientales departement typical climatic conditions. Experimentations on the same orchard in Elne, Pyrénées-Orienteles department, with winter chilling requirement below 7.2° C. comprised between 700 hours and 1200 hours according to the specificities of the year, namely 1031 hours in 2012-2013, 777 hours in 2013-2014, 893 hours in 2014-2015, 718 hours in 2015-2016, 825 hours in 2016-2017, 1017 hours in 2017-2018 and 844 hours in 2018-2019 showed a good behaviour of the trees in all cases. Traditionally, flat fruits are more sensitive to critical low temperatures and to climatic variations, because of the flower morphology in which the ovule is less protected than in the classical round fruits. Thus, areas not much exposed to frost are recommended for trees growth. However, 'FLATRUMBA' trees seem to be very resistant to critical frosty weather.

Trunk:

*Diameter.*—Approximately 36.0 to 40.0 millimeters in diameter when measured at a distance of approximately 20.0 centimeters above the soil level in their third growing season (second year of production).

*Bark texture.*—Considered rough, with lenticels.

*Lenticels.*—Numerous lenticels are present. The number of lenticels reaches 2 lenticels per $cm^2$. The lenticels range in size of approximately 3.0 to 4.0 millimeters in width, and about 1.0 to 1.5 millimeters in height.

*Lenticel color.*—The lenticels show a light orange color (RHS Greyed Orange 165 B or RHS Greyed Orange 165 C).

*Bark coloration.*—The bark has a brown to grey color (RHS Grey 201 A or RHS Grey 201 B) darker than the lenticels color.

Branches:

*Size.*—The branches are pruned to approximately 1.0 meter in length.

*Diameter.*—Average as compared to other peach varieties. The current season shoots have a diameter of approximately 4.0 to 6.0 millimeters, and mature branches have a diameter of approximately 7.0 to 9.0 millimeters.

*Surface texture.*—Smooth for current season shoots and rough, with lenticels, for mature branches, wood which is several years old has no furrowed appearance.

*Crotch angles.*—Primary branches are considered variable, but the crotch angles are generally 45 degrees from the horizontal axis for current season shoots and 60° degrees from the horizontal axis for mature branches. This particular characteristic is not considered distinctive of the variety, however.

*Current season shoots.*—

*Internode length.*—Generally 21.0 to 24.0 millimeters.

*Color.*—The color of new shoot tips is considered light green (RHS Yellow Green 145 A) on lower part of new shoot tips, whereas the upper part is darker and colored in purple (RHS Greyed Purple 183 A or RHS Greyed Purple 183 B), depending on the level on the tip and the sunlight exposure.

*Mature branches.*—

*Internode length.*—Generally 16.0 to 22.0 millimeters.

*Color of mature branches.*—Brown (RHS Grey Brown N 199 B or RHS Grey Brown N 199 C).

*Lenticels.*—Numerous lenticels are present on mature branches. The number of lenticels reaches 6 lenticels per $cm^2$. The size of lenticels is considered small. The lenticels range in size from approximately 1.0 millimeter in width, and about 0.5 millimeters in height. The lenticel shape is round and slightly stretched.

*Lenticel color.*—The lenticels on mature branches have a beige color (RHS Greyed Orange 164 C).

Leaves:

*Size.*—Considered medium for the species. The ratio leaf length/leaf width is 3.84.

*Leaf length.*—Approximately 164.0 to 196.0 millimeters with leaf petiole. The medium length is about 177.2 millimeters with leaf petiole.

*Leaf width.*—Approximately 40.0 to 50.0 millimeters. The medium width is 46.2 millimeters.

*Leaf form (in cross section).*—Concave.

*Leaf form.*—Lanceolate.

*Leaf base shape.*—Acute.

*Leaf tip form.*—Acuminate, short and pointed (acute).

*Leaf thickness.*—Medium.

*Leaf color.*—

*Upper leaf surface.*—Yellow Green (RHS Yellow Green 147 A).

*Lower surface.*—A slightly lighter green (RHS Yellow Green 147 B) than the upper leaf surface color.

*Leaf texture.*—Smooth and glabrous on both upper and lower surfaces of the leaf.

*Leaf venation.*—Pinnately veined.

*Mid-vein.*—

*Color.*—Light green, almost cream white (RHS Yellow Green 145 A or RHS Yellow Green 150 D). The color may evolve with maturity.

*Width.*—Approximately 1.5 millimeters.

*Secondary veins.*—

*Color.*—Light green (RHS Yellow Green 145 C or RHS Yellow Green 145 D). Mid-vein and secondary veins are embossed on lower surface of the leaves but are apparent on upper surface too.

*Red mid-vein on the lower leaf surface.*—Absent.

*Leaf margins.*—Slightly undulating.

*Leaf margin form.*—Leaf margins are considered slightly dentate or crenate.

*Uniformity.*—Leaves are isolated or grouped by 2 or 3. In this last case, one leaf of normal size is found with one or two smaller leaves (at least 50% smaller).

*Leaf petioles.*—

*Size.*—Considered medium.

*Length.*—About 10.0 to about 13.0 millimeters.

*Diameter.*—About 1.5 to 2.0 millimeters.

*Shape.*—Grooved.

*Petiole color.*—

*Upper petiole surface.*—Green (RHS Yellow Green 144 B).

*Lower surface.*—Light green (RHS Yellow Green 145 B or RHS Yellow Green 144 D).

*Leaf glands.*—

*Size.*—Considered medium. Their length is about 1.0 millimeter and their width is about 1.0 millimeter.

*Number.*—Generally 2 or 3 glands per leaf.

*Type.*—Round.

*Margins.*—Smooth and regular.

*Position.*—Alternate on the upper part of petiole.

*Color.*—On young leaves, leaf glands color is considered a light green (RHS Green 145 B). On older leaves, leaf glands color turns to a dark brown (RHS Grey Brown 199 A or RHS Grey Brown 199 B or RHS Brown 200 A).

*Leaf stipules.*—

*Generally.*—No leaf stipules were observed. But as seen in the characteristic relative to the leaves uniformity, it is possible to find leaves by groups of 2 or 3, with a normal-size leaf and smaller ones.

*Presence and intensity of flowering shoot anthocyanin coloration.*—A greyed purple color (RHS Greyed Purple 185 B) is present on the upper part, i.e the surface which is exposed to the sun, of the shoots.

*Time of beginning of leaf bud burst.*—Considered medium.

Flowers:

*Flower buds.*—

*Generally.*—At pre-floral stage of development, the floral buds are conic in form with a round tip. Their form is evolving until blooming, with variable dimensions. Just before blooming, floral buds are approximately 10.0 to 11.0 millimeters wide and approximately 16.0 to 18.0 millimeters long.

*Color.*—This characteristic is dependent upon the proximity to bloom. At pre-floral stage of development, the bottom of the flower's buds, or calyx, or flower receptacle, is of purple brown color (RHS Greyed Purple 183 A). The corolla, formed by the petals, is generally of pink color (RHS Red Purple 73 C or RHS Red Purple 73 D) on both faces. Petals color shows an evolution until the end of flowering.

*Hardiness.*—The buds are considered hardy under typical central Pyrénées-Orientales departement climatic conditions. No winter injury was noted during the last several years of evaluation in the central Pyrénées-Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

*Date of bloom.*—The blooming time generally begins at the end of February or early in March. The first bloom was observed on Feb. 22, 2016.

*Blooming time.*—Considered medium in relative comparison to other commercial peach cultivars grown in the Pyrénées-Orientales departement, France. The date of full bloom is observed generally at the middle of the blooming period. The date of bloom varies slightly with climatic conditions and cultural practices. Thus, the full bloom was observed in 2016, from February $22^{nd}$ until March $5^{th}$, then from March $4^{th}$ until Mar. 9, 2017, then from March $2^{nd}$ until Mar. 7, 2018 and then from March $3^{rd}$ until Mar. 13, 2019.

*Duration of bloom.*—Medium, approximately between 6 to 13 days. This characteristic varies slightly with the prevailing climatic conditions.

*Flower type.*—The variety is considered to have a showy type flower.

*Flower size.*—Considered medium. Flower diameter at full bloom is approximately 32.0 to 35.0 millimeters.

*Bloom quantity.*—Considered medium, approximately between 30 and 35 flowers per meter, with a high rate of fruit set.

*Flower bud frequency.*—Generally 2 flower buds appear per node, occasionally 1.

*Petal size.*—

*Generally.*—Considered medium.

*Length.*—Generally between 18.0 and 19.0 millimeters.

*Width.*—Generally between 17.0 and 19.0 millimeters.

*Petal form.*—Round-shaped.

*Petal count.*—Generally 5.

*Petal texture.*—Smooth, soft and glabrous on both upper and lower surfaces of the petal.

*Petal color.*—At the stage F of blooming, when the flower is fully opened, both surfaces of the petal are colored with a dark pink (RHS Red Purple 73 B or RHS Red Purple 73 C) when young, becoming slightly darker until the end of blooming. Stage F of blooming corresponds to the stage of flowering where the flower is fully opened. Petal color may show an evolution during the flowering, from the pre-floral stage we previously described, until the end of flowering.

*Fragrance.*—Sweet.

*Petal claw.*—

*Form.*—The claw is considered to have a narrow form.

*Length.*—About 1.5 millimeters.

*Width.*—About 1.5 millimeters at the base.

*Color.*—The petal claw usually shows a pink color darker than the petal color (RHS Red 51 A to RHS Red 51 B).

*Petal margins.*—Generally considered slightly undulating.

*Petal apex.*—

*Generally.*—The petal apices are generally shaped as a wide dome.

*Flower pedicel.*—

*Length.*—Considered medium and having an average length of approximately 3.0 millimeters.

*Diameter.*—Considered average, approximately 1.5 millimeters.

*Color.*—Light green (RHS Yellow Green 145 A or RHS Yellow Green 145 B).

*Calyx.*—

*Internal surface texture.*—Smooth and glabrous.

*Color.*—At the stage F of blooming, when the flower is opened, the inner surface of the calyx, namely the flower receptacle, is greenish yellow (RHS Yellow Green 153 C or RHS Yellow Green 153 D). The outer surface of the calyx is considered of purple brown color (RHS Greyed Purple 183 A) and light green near the base (RHS Yellow Green N144 A or RHS Yellow Green N144 B). Stage F of blooming corresponds to the stage of flowering where the flower is fully opened. Calyx color, just as petal color, may show an evolution during the flowering, from the pre-floral stage we previously described, until the end of flowering.

*Sepals.*—

*Sepal count.*—5.

*Surface texture.*—The outer surface has a short, fine pubescent texture. The inner surface has a smooth texture.

*Margins.*—Smooth.

*Size.*—Medium to small.

*Length.*—Approximately 4.0 to 5.0 millimeters.

*Width.*—Approximately 4.0 to 5.0 millimeters.

*Form.*—Conic and round at the top.

*Color.*—The upper surface of the sepals shows a purple color (RHS Greyed Purple 183 A) whereas the lower surface of sepals is considered greenish yellow (RHS Yellow Green 153 C or RHS Yellow Green 153 D).

*Anthers.*—

*Generally.*—Medium in length.

*Shape.*—Cordate.

*Color.*—At an early stage of maturity, anthers are colored with an orange yellow (RHS Yellow Orange 16 A or RHS Yellow Orange 16 B) or an orange red color (RHS Orange Red N 34 A or RHS Greyed red Group 178 A). The color of the anthers evolves with maturity.

*Pollen production.*—Pollen is abundant and has an orange yellow color (RHS Yellow Orange 17 B or RHS Yellow Orange 17 C) which may evolve with maturity. The present variety is considered auto-fertile (self-pollinating).

*Filaments.*—

*Size.*—Medium length, between 10.0 and 13.0 millimeters in length. Filaments length is generally slightly higher than the pistil's length.

*Color.*—Considered pale pink (RHS Red Purple 62 C or RHS Red Purple 62 D) or a slightly darker pink (RHS Red Purple 73 A or RHS Red Purple 73 B). The color becomes darker at the end of blooming.

*Average number of stamens per flower.*—Generally between 34 and 38.

*Pistil.*—

*Number.*—Usually 1.

*Generally.*—Average in size.

*Length.*—Approximately 12.0 to 14.0 millimeters including the ovary. Generally smaller than filaments in length when considered without the ovary.

*Color.*—Considered a very pale green (RHS Yellow Green Group 151 D) at the beginning of blooming period. The color evolves during the blooming to become more and more pale green (RHS Yellow Green 150 D) and sometimes very slightly pink (RHS Red Group 36 D) at the end of blooming.

*Ovary.*—

*Pubescence.*—Present.

*Stamen.*—Size compared to petals.—The size of stamen is smaller than the size of petals.

*Stigma.*—

*Position compared to anthers.*—The stigma is below the anthers.

Fruit:

*Maturity when described.*—Very firm in ripe conditions (shipping ripe).

*Date of first picking.*—Aug. 22, 2015.

*Date of last picking.*—The date of harvest varies slightly with the prevailing climatic conditions. The 'FLATRUMBA' variety has a late date of picking, and a grouped maturity. The maturity is grouped within 7 to 11 days and the harvest is generally performed in two runs. Last known picking times carry on from August 22$^{nd}$ to Aug. 28, 2015, then from August 22$^{nd}$ to Aug. 28, 2016, then from August 21$^{st}$ to Aug. 27, 2017, and then from August 23$^{rd}$ to Sep. 2, 2018.

*Size.*—

*Generally.*—Homogeneous in size, size 3A considering the European Regulation related to commercialization of fruits. Considered large, with a diameter generally between 80 and 90 millimeters.

*Average cheek diameter.*—Approximately 78.0 to 83.0 millimeters.

*Average axial diameter.*—Approximately 48.0 to 54.0 millimeters.

*Typical weight.*—Approximately 180 to 200.0 grams. This characteristic is high dependent upon the prevailing cultural practices, and therefore is not particularly distinctive of the variety.

*Fruit form.*—

*Generally.*—Round and flattened, generally with few bump, slightly cordate. The fruit is generally uniform in symmetry, viewed from the suture's plane, sometimes asymmetrical.

*Suture.*—

*Fruit suture.*—The suture is usually absent, or wide-mouthed and slightly marked when present, extending from the base to the apex. No apparent callousing or stitching exists along the suture line. Not pointed.

*Color.*—When present, the suture has generally a similar color to the whole fruit color, which is purple red (RHS Greyed Purple 183 A or RHS Greyed Purple 183 B).

*Ventral surface.*—

*Form.*—Smooth.

*Apex.*—Slightly depressed.

*Base.*—Semi-flared, shallow.

*Mucron.*—Absent.

*Closing of the pistil cavity.*—Very good.

*Stem cavity.*—Average depth of the stem cavity is considered small, about 8.0 to 11.0 millimeters. Average width is between 14.0 and 18.0 millimeters.

*Fruit skin.*—

*Thickness.*—Considered medium thick and strong, and the adherence of skin to flesh is strong to medium, depending on the fruit maturity.

*Texture.*—Very smooth and almost glabrous for a peach variety, the pubescence of the skin is almost non-existent. However, the peach variety named 'FLATRUMBA', has a skin pubescence, even the latter being very thin.

*Taste.*—Semi-sweet, sugary.

*Tendency to crack.*—None observed.

*Color.*—

Figure 3:
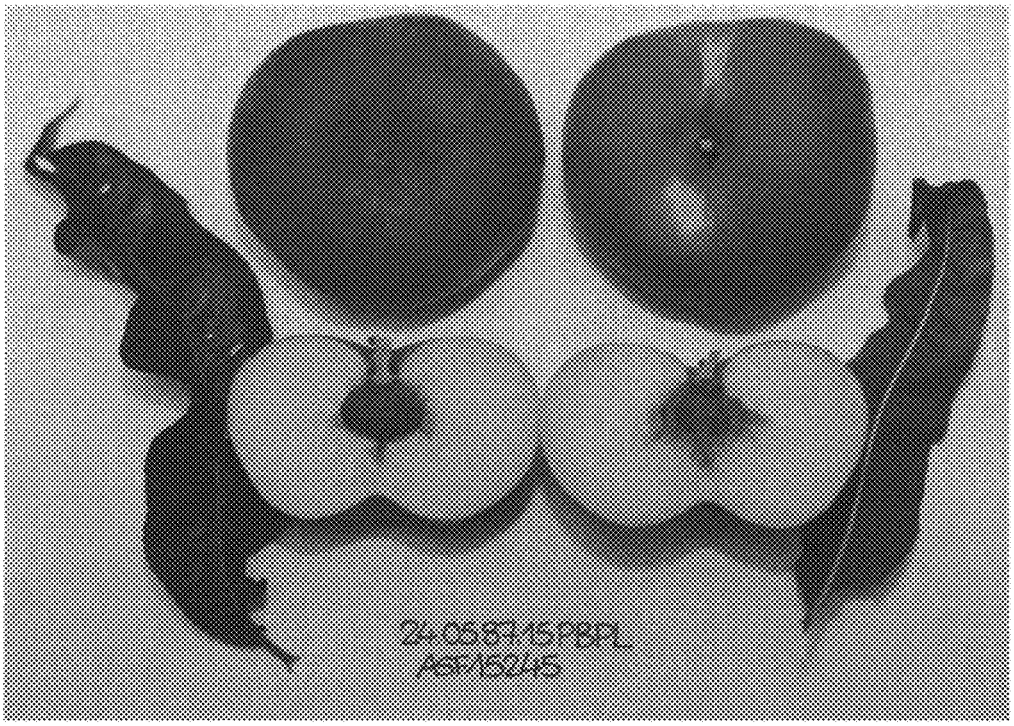
FIG. 3 is a color photograph which shows the upper and lower sides of leaves and different views of three typical specimens of the fruit of the new variety 'FLATRUMBA' at ripening time, one fruit having been cut in half with the pit being left in one of the halves for depicting leaves, fruit flesh, pit and pit cavity of the new variety which is also referenced '24.05.87.15 PBPL ASF15245' by the breeder.
Figure 4:
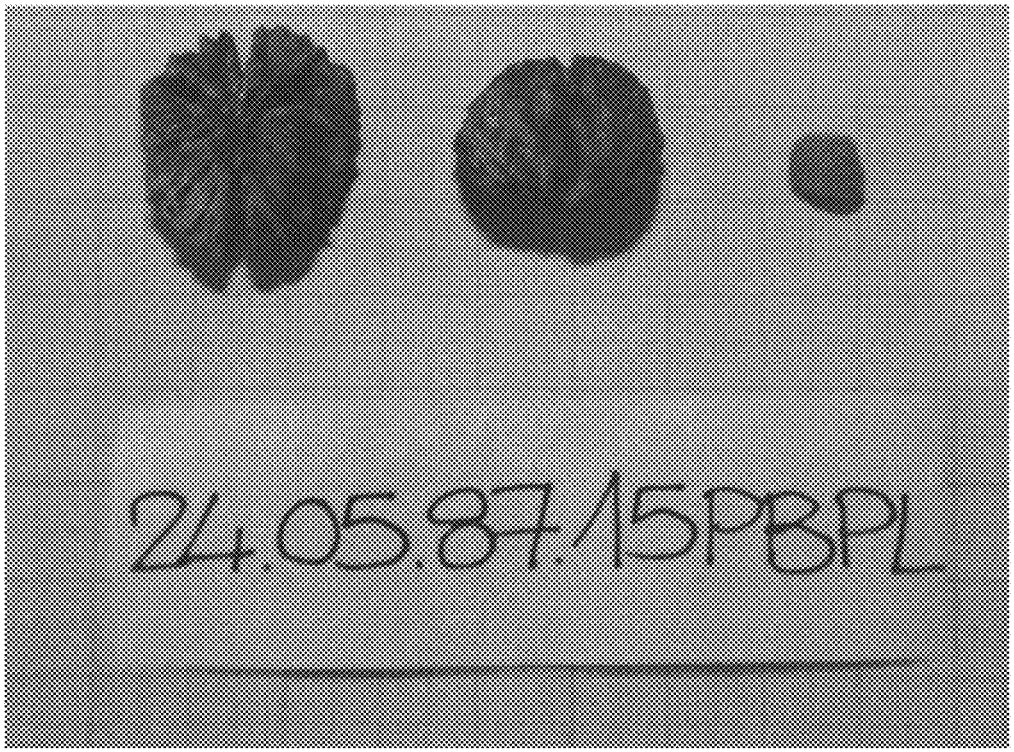
FIG. 4 is a color photograph that shows different views of the stone of the new variety which is also referenced '24.05.87.15 PBPL' on this figure, and the kernel of the stone.

*Blush color.*—This blush color is a luminous purple red (RHS Greyed Purple 183 A or RHS Greyed Purple 183 B). The purple red blush covers approximately 75% of the fruit skin surface on a washed red background (RHS Greyed Red 179 A or RHS Greyed Red 179 B) on approximately 25% of the fruit skin surface. The percentage of the blush on the fruit skin surface can vary and is generally dependent upon the prevailing conditions under which the fruit was grown. FIG. 3 is a color photograph which shows fruit skin of the new variety 'FLATRUMBA' at ripening time. As one can observed on this figure, a couple of yellow blotches at the stalk end of the fruit are present. These blotches are however not a distinctive characteristic which is present on every fruit of the new variety and may correspond to a trace which has been left by branches on young trees. It has been noted that this default tends to disappear on older trees.

*Ground color.*—The ground color covers approximately 25% of the fruit skin surface, and is considered washed red (RHS Greyed Red 179 A or RHS Greyed Red 179 B).

*Lenticels.*—None.

*Fruit stem.*—Medium in length, approximately 7.0 to 10.0 millimeters.

*Diameter.*—Approximately 4.0 to 5.0 millimeters.

*Color.*—Pale green (RHS Yellow Green 145 A).

*Flesh.*—

*Ripens.*—Very homogenously, slowly. The flesh has a long shelf life.

*Texture.*—Very firm, very dense, crunchy, melting, juicy at harvest maturity stage.

*Fibers.*—Not fibrous.

*Aroma.*—Considered present to very pronounced.

*Eating quality.*—Considered very good, aromatic.

*Flavor.*—Considered sweet to semi-sweet. The Brix is generally superior to 13, and sometimes reaches 18, and acidity is comprised between 6 and 9 meq/100 ml.

*Juice.*—Juicy to very juicy at complete maturity.

*Brix.*—Generally between 13.5 and 15.0 degrees. Sometimes, the Brix reaches 18.0 degrees. This characteristic varies slightly with the number of fruit per tree; prevailing cultural practices; and the surrounding climatic conditions.

*Flesh color.*—The flesh is considered white (RHS Green White 157 C or RHS Green White 157 D) or cream white (RHS White 155 A or RHS White 155 B), usually with a red pigmentation (RHS Red 47 A) into the stone cavity and in a star shape around the stone cavity, on approximately 5.0 to 6.0 millimeters, which can been seen on FIG. 3 when the fruit is cut transversely.

Stone:

*Type.*—Semi-Clingstone, more or less semi-adherent depending on the fruit maturity.

*Size.*—Considered small for the variety. The stone size varies significantly depending upon the tree vigor, crop load and prevailing growing conditions.

*Length.*—Approximately 14.0 to 15.0 millimeters.

*Width.*—Approximately 23.0 to 24.0 millimeters.

*Diameter.*—Approximately 22.0 to 23.0 millimeters.

*Form.*—Flattened.

*Base.*—Straight.

*Apex.*—

*Shape.*—The stone apex is flattened.

*Stone cavity.*—Considered small size, with flattened form and dimensions corresponding to the stone's dimensions.

*Stone surface.*—

*Surface texture.*—The pit is transversely furrowed on its entire surface. Furrows are deeper and more oblate on lateral sides.

*Ridges.*—The surface texture is generally characterized by more prominent ridges along the ventral edges and at the apical tip.

*Ventral edge.*—

*Width.*—Approximately 3.0 to 4.0 millimeters at mid-suture.

*Dorsal edge.*—

*Shape.*—Grooved.

*Stone color.*—The color of the dry stone is generally considered orange brown (RHS Greyed Orange 164 B or RHS Greyed Orange 164 C).

*Tendency to split.*—Splitting is absent.

*Kernel.*—

*Size.*—The kernel is considered small.

*Length.*—Approximately 9.0 millimeters.

*Width.*—Approximately 8.0 millimeters.

*Thickness.*—Approximately 7.0 millimeters.

*Form.*—Considered flattened and elliptic. Sometimes double.

*Pellicle.*—The pellicle of the kernel has a short pubescence.

*Color.*—The kernel skin is orange-brown colored (RHS Greyed Orange N167 A). The almond, which is the seed of the kernel, is white (RHS White 155 A) and has a bitter taste. The kernel and its embryo are mature at the time of fruit maturity.

*Use.*—The subject variety 'FLATRUMBA' is considered to be a white flat peach tree having a late season of maturity, and which produces fruits that are considered firm, attractively colored in purple red. Fruits have a semi-sweet taste and are excellent for uncooked consumption, crunchy or melting when at full maturity. Fruits have excellent gustative qualities. Due to their flesh quality, firmness and density, they can also be commercialized as $4^{th}$ range product (packed fruit or fruit in bags for example). And they are also useful for both local and very long-distance shipping.

*Keeping quality.*—Remarkable. Fruit have a slow maturation and a long shelf life both on the tree after growth completion and after harvesting without alteration. After growth completion, fruits are preserved more than one week. After harvest, fruits are well preserved more than 2 weeks at 2.0 degree Celsius.

*Shipping quality.*—Considered very good. The fruit of the new white flat peach variety showed minimal bruising of the flesh or skin damage after being subjected to normal harvesting and packing procedures. Its resistance to handling during harvest and packing and its long shelf life without alteration after harvest easily permit 2 weeks-shipping at 2 degrees Celsius.

*Resistance to insects and disease.*—No particular susceptibilities were noted. The present variety is not very sensitive to *Monilia* or rot. The pistil cavity is completely closed, generally without any cork formation.

Although the new variety of white flat peach tree possesses the described characteristics when grown under the ecological conditions prevailing near Elne, Pyrénées-Orientales departement, France, it should be understood that variations of the usual magnitude and characteristics incident to changes in growing conditions, fertilization, pruning, pest control and horticultural management are to be expected.

We claim:

1. A new and distinct variety of white flat peach tree as illustrated and described, characterized by fruits with high eating quality and very long shelf life without alteration before and after harvesting, with a semi-sweet white or cream white flesh, a red pigmentation into and around the stone cavity, and an attractive skin with a high percentage of luminous purple red blush on skin surface, on a washed red background.

* * * * *